(12) United States Patent
Mizukami et al.

(10) Patent No.: US 10,567,706 B2
(45) Date of Patent: Feb. 18, 2020

(54) RELAY DEVICE AND MEDICAL DEVICE

(71) Applicant: SONY OLYMPUS MEDICAL SOLUTIONS INC., Tokyo (JP)

(72) Inventors: Aki Mizukami, Kanagawa (JP); Yoshihiro Koizumi, Tokyo (JP); Masashige Kimura, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 15/558,088

(22) PCT Filed: Feb. 22, 2016

(86) PCT No.: PCT/JP2016/055115
§ 371 (c)(1),
(2) Date: Sep. 13, 2017

(87) PCT Pub. No.: WO2016/174902
PCT Pub. Date: Nov. 3, 2016

(65) Prior Publication Data
US 2018/0048856 A1  Feb. 15, 2018

(30) Foreign Application Priority Data
Apr. 30, 2015 (JP) .................. 2015-093676

(51) Int. Cl.
*H04N 7/10* (2006.01)
*G02B 23/24* (2006.01)
(Continued)

(52) U.S. Cl.
CPC ............... *H04N 7/102* (2013.01); *A61B 1/00* (2013.01); *A61B 1/04* (2013.01); *G02B 23/24* (2013.01);
(Continued)

(58) Field of Classification Search
CPC ............ A61B 1/00006; A61B 1/00009; A61B 1/00013; A61B 1/00018; A61B 1/00;
(Continued)

(56) References Cited

U.S. PATENT DOCUMENTS

| 2010/0064082 A1* | 3/2010 | Ihle | H04L 12/40013 |
| | | | 710/106 |
| 2010/0262920 A1* | 10/2010 | Tischer | H04L 12/66 |
| | | | 715/745 |

(Continued)

FOREIGN PATENT DOCUMENTS

| CN | 103731606 A | 4/2014 |
| CN | 104335192 A | 2/2015 |

(Continued)

OTHER PUBLICATIONS

International Search Report dated May 24, 2016, in PCT/JP2016/055115 filed Feb. 22, 2016.

(Continued)

*Primary Examiner* — Loi H Tran
(74) *Attorney, Agent, or Firm* — Xsensus LLP

(57) ABSTRACT

An interface module 61 relays control signal communication between a main CPU 621 and a light source control CPU 651 and between the main CPU 621 and a camera head CPU 242. The interface module 61 includes an FPGA 610 having CPU I/Fs 611 to 613 that correspond to communication schemes of CPUs 621, 651, and 242, respectively, and first and second storage units 615 (617) and 616 (618). The FPGA 610 relays a control signal between the main CPU 621 and the light source control CPU 651 and between the main CPU 621 and the camera head CPU 242, while temporarily storing the control signal in the first and the second storage units 615 (617) and 616 (618). Moreover, a first communication timing and second and third communication timings are set at timings shifted from one another.

3 Claims, 4 Drawing Sheets

(51) Int. Cl.
*A61B 1/04* (2006.01)
*A61B 1/00* (2006.01)
*H04N 5/77* (2006.01)
*A61B 1/045* (2006.01)

(52) U.S. Cl.
CPC ............ *H04N 5/77* (2013.01); *A61B 1/00006* (2013.01); *A61B 1/00009* (2013.01); *A61B 1/00013* (2013.01); *A61B 1/00018* (2013.01); *A61B 1/045* (2013.01)

(58) Field of Classification Search
CPC .......... A61B 1/04; A61B 1/045; G02B 23/24; H04N 5/77; H04N 7/102
USPC .......................................................... 348/75
See application file for complete search history.

(56) References Cited

U.S. PATENT DOCUMENTS

| | | | | |
|---|---|---|---|---|
| 2012/0185268 | A1* | 7/2012 | Wiesner | G06F 19/3418 |
| | | | | 705/2 |
| 2013/0028222 | A1* | 1/2013 | Nakasato | H04W 36/08 |
| | | | | 370/329 |
| 2013/0141557 | A1 | 6/2013 | Kawata et al. | |
| 2013/0332633 | A1* | 12/2013 | Carney | G06F 13/4291 |
| | | | | 710/48 |
| 2014/0078278 | A1 | 3/2014 | Lei | |

FOREIGN PATENT DOCUMENTS

| | | |
|---|---|---|
| JP | 7-303652 A | 11/1995 |
| WO | WO 2012/132096 A1 | 10/2012 |
| WO | WO 2013/108873 A1 | 7/2013 |
| WO | WO 2013/184294 A1 | 12/2013 |
| WO | WO 2014/081512 A1 | 5/2014 |

OTHER PUBLICATIONS

Combined Chinese Office Action and Search Report dated Jan. 23, 2019 in Patent Application No. 2016800233297 (with English translation) citing documents AO and AP therein, 13 pages.
Extended European Search Report dated Sep. 20, 2018 in corresponding European Patent Application No. 16786179.8 citing documents AA and AO therein, 7 pages.

\* cited by examiner

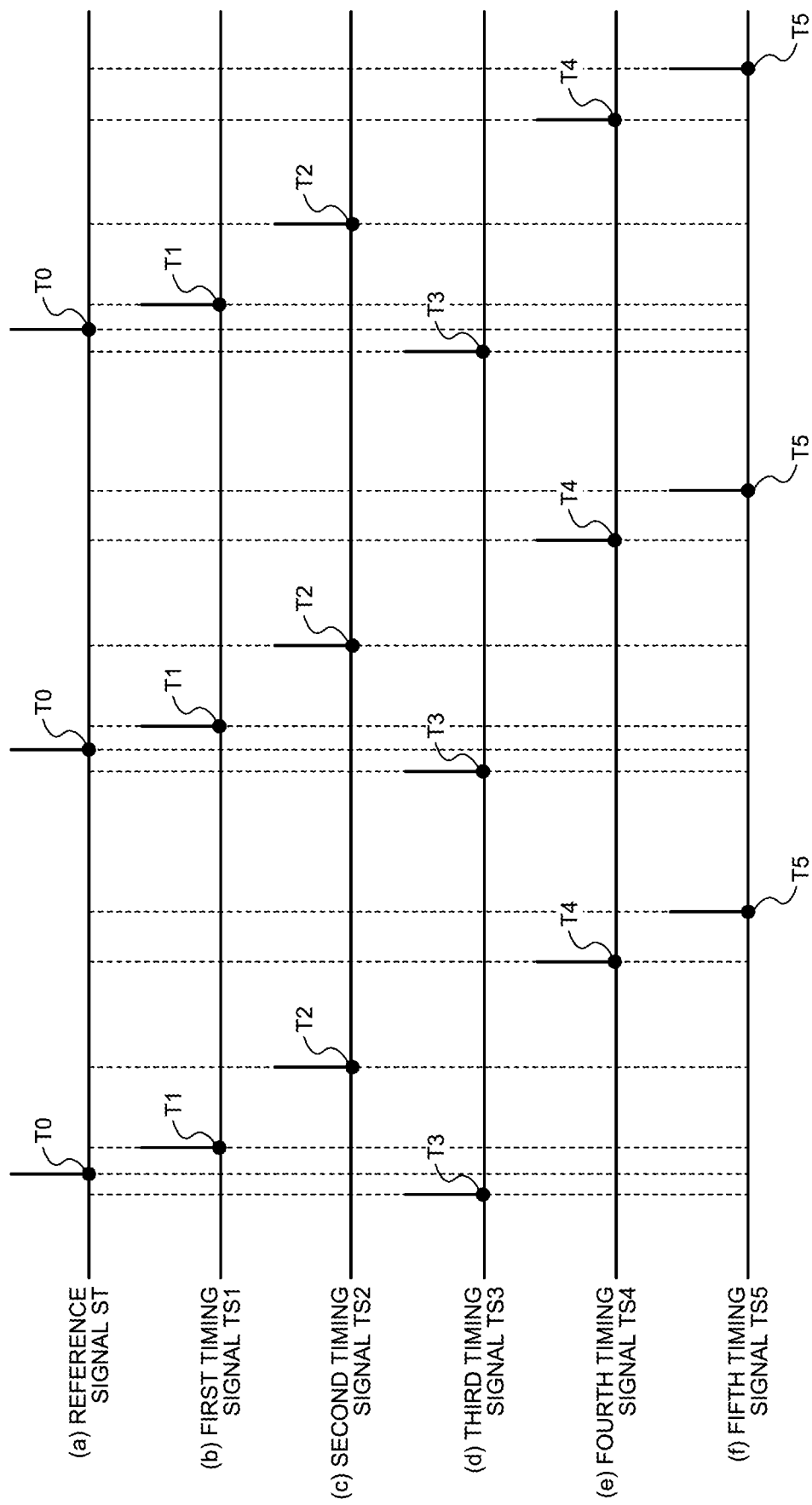

RELAY DEVICE AND MEDICAL DEVICE

FIELD

The present invention relates to a relay device and a medical device.

BACKGROUND

Conventionally, a medical device including a first device and a plurality of second devices that each perform control signal communication with the first device has been known (for example, see Patent Literature 1).

In the medical device (medical endoscope system) disclosed in Patent Literature 1, the first device (central processing unit (CPU) in the system controller) and each of the second devices (CPUs in a camera device for an endoscope, a light source device, and the like) are connected one-by-one by a dedicated communication line. The first device functions as a master, and the first device centrally controls the second devices.

CITATION LIST

Patent Literature

Patent Literature 1: Japanese Laid-open Patent Publication No. 7-303652

SUMMARY

Technical Problem

In the medical device disclosed in Patent Literature 1, the first device and each of the second devices are connected one-by-one by a dedicated communication line. When such a configuration is used, the first device needs to hold a plurality of communication interfaces so that the first device can correspond to all communication schemes (communication standards) of the second devices. In other words, a special first device with the communication interfaces as described above needs to be selected, while configuring a medical device. As a result, freedom in selecting a device is restricted.

The present invention has been made in view of the above, and an object of the present invention is to provide a relay device and a medical device that can improve the freedom in selecting a device, while configuring a medical device.

Solution to Problem

To solve the above-described problem and achieve the object, a relay device according to the present invention is a relay device for being used in a medical device including a first device and a plurality of second devices, the second devices each performing control signal communication with the first device, and for relaying the control signal communication between the first device and the second devices, and the relay device includes: a programmable logic device including: a first interface unit configured to communicate with the first device in a communication scheme corresponding to a communication scheme of the first device; and a plurality of second interface units each configured to perform communication with the respective second devices in communication schemes corresponding to communication schemes of the second devices; and a plurality of pairs of a first storage unit and a second storage unit, wherein the pairs of the first storage unit and the second storage unit are provided in each of the second interface units, the programmable logic device temporarily stores a control signal received from the first device via the first interface unit in the first storage unit at a first communication timing, and transmits the control signal to the second device via the second interface unit at a second communication timing, and temporarily stores a control signal received from the second device via the second interface unit in the second storage unit at a third communication timing, and transmits the control signal to the first device via the first interface unit at the first communication timing, and the first communication timing and the second and the third communication timings are set at timings shifted from one another.

In the above-described relay device according to the present invention, the first communication timing, the second communication timing, and the third communication timing are changeable.

In the above-described relay device according to the present invention, the pairs of the first storage unit and the second storage unit are provided inside the programmable logic device.

A medical device according to the present invention includes: a first device; a plurality of second devices that each perform control signal communication with the first device; and the above-described relay device configured to relay control signal communication between the first device and the second devices.

Advantageous Effects of Invention

The relay device according to the present invention relays control signal communication between the first device and the second devices. The relay device includes the programmable logic device that has the first interface unit corresponding to the communication scheme of the first device, and the second interface units corresponding to the respective communication schemes of the second devices.

Thus, when the relay device is used to relay the control signal communication between the first device and the second devices, it is possible to configure a medical device at a low cost, compared to the conventional configuration in which a special first device with a plurality of communication interfaces is used. Moreover, it is possible to improve the freedom in selecting a device, while configuring the medical device.

Furthermore, the relay device according to the present invention includes the pairs of the first and the second storage units that are provided in each of the second interface units (second devices). The programmable logic device relays control signals between the first device and the second devices, at the first communication timing to the third communication timing described above, while temporarily storing the control signal in the pairs of the first and the second storage units. Still furthermore, the first communication timing and the second and the third communication timings are set at timings shifted from one another.

Hence, the timing at which the control signal is written and the timing at which the control signal is read out will not coincide (crash) with each other, in each of the first and the second storage units. In other words, even if the relay device is used to relay the control signals between the first device and the second devices, a communication error will not occur between the first device and the second devices. Thus, it is possible to sufficiently achieve communication reliability.

The medical device according to the present invention includes the relay device described above, and has the same effects as those of the relay device described above.

BRIEF DESCRIPTION OF DRAWINGS

FIG. 4 is a timing chart illustrating an example of a reference signal used in an FPGA illustrated in FIG. 3, and a first timing signal to a fifth timing signal generated by the FPGA.

DESCRIPTION OF EMBODIMENTS

Figure 1:
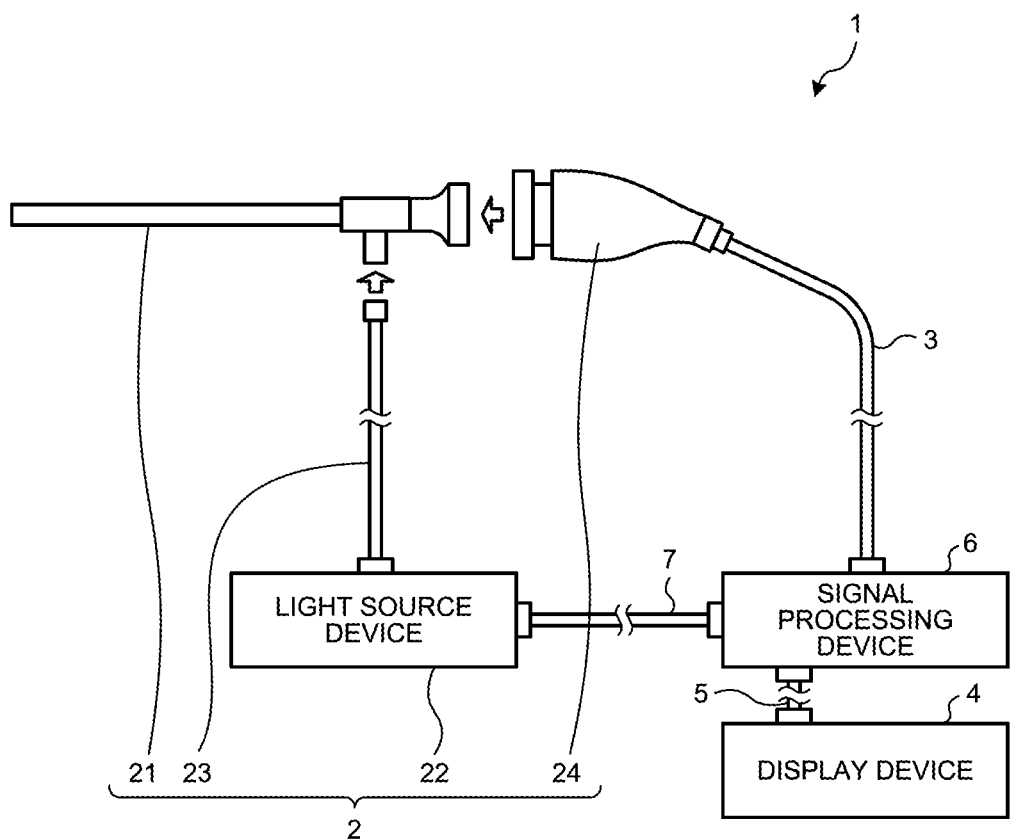
FIG. 1 is a diagram illustrating a schematic configuration of a medical observation system according to an embodiment of the present invention.

Hereinafter, a mode for carrying out the present invention (hereinafter, embodiment) will be described in detail with reference to the accompanying drawings. It is not intended that the present invention be limited by what has been described in the following embodiment. Moreover, in the drawings, the same reference numerals denote the same components.

Schematic Configuration of Medical Observation System

FIG. 1 is a diagram illustrating a schematic configuration of a medical observation system 1 according to an embodiment of the present invention.

The medical observation system 1 functions as a medical device according to the present invention.

The medical observation system 1 is a system used in the medical field, and observes the inside of a subject (inside of a living body) such as human. As illustrated in FIG. 1, the medical observation system 1 includes an endoscope 2, a first transmission cable 3, a display device 4, a second transmission cable 5, a signal processing device 6, and a third transmission cable 7.

The endoscope 2 examines the inside of the living body and outputs a signal corresponding to the examination result. As illustrated in FIG. 1, the endoscope 2 includes an insertion unit 21, a light source device 22, a light guide 23, and a camera head 24.

The insertion unit 21 is hard, has an elongated shape, and is inserted into the living body. An optical system that is formed of a single or a plurality of lenses and that condenses an image of a subject is provided inside the insertion unit 21.

An end of the light guide 23 is connected to the light source device 22, and under the control of the signal processing device 6, the light source device 22 supplies light for illuminating the inside of the living body to the end of the light guide 23.

The end of the light guide 23 is detachably connected to the light source device 22, and the other end of the light guide 23 is detachably connected to the insertion unit 21. The light guide 23 transmits the light supplied from the light source device 22 from one end to the other end, and supplies the light to the insertion unit 21. The light supplied to the insertion unit 21 is output from the tip end of the insertion unit 21, and applied to the inside of the living body. The light applied to the inside of the living body (image of the subject) is condensed by the optical system in the insertion unit 21.

The camera head 24 is detachably connected to a base end of the insertion unit 21. The camera head 24 includes an image pickup unit 241 (see FIG. 2), a camera head CPU 242 (see FIG. 2), and the like.

Under the control of the camera head CPU 242, the image pickup unit 241 takes an image of the inside of the living body. The image pickup unit 241 includes a sensor chip in which an image pickup element (not illustrated), a signal processing unit (not illustrated), and the like are integrally formed. The image pickup element is a charge coupled device (CCD), a complementary metal oxide semiconductor (CMOS), or the like, and receives the image of the subject that is condensed by the insertion unit 21 and that is formed by the optical system (not illustrated) provided inside the camera head 24. The image pickup element then converts the image of the subject to an electrical signal. The signal processing unit performs signal processing (such as analog-to-digital (A/D) conversion) on the electrical signal (analog signal) from the image pickup element, and outputs an image pickup signal.

In the present embodiment, the camera head 24 photoelectrically converts the image pickup signal to an optical signal, and outputs the image pickup signal as the optical signal.

The camera head CPU 242 functions as a second device according to the present invention. The camera head CPU 242 controls the overall operation of the camera head 24, according to a control signal that is received from the signal processing device 6 via the first transmission cable 3, and a user operation on an operation unit (not illustrated) such as a switch that is provided on the outer surface of the camera head 24 in an exposed manner, on the basis of various programs recorded in an internal memory (not illustrated).

In the present embodiment, the camera head CPU 242 includes a CPU that performs communication according to a universal asynchronous receiver transmitter (UART) standard.

An end of the first transmission cable 3 is detachably connected to the signal processing device 6, and the other end of the first transmission cable 3 is detachably connected to the camera head 24. More specifically, the first transmission cable 3 is a cable made of a plurality of electrical wirings (not illustrated) and optical fibers (not illustrated) being disposed inside the outer coat that is the outermost layer.

The electrical wirings are electrical wirings for transmitting a control signal, a synchronization signal, a clock, power, and the like that are output from the signal processing device 6 to the camera head 24.

The optical fibers are optical fibers for transmitting the image pickup signal (optical signal) output from the camera head 24 to the signal processing device 6. In this example, when the image pickup signal is output from the camera head 24 as the electrical signal, the optical fibers may be replaced with the electrical wirings.

The display device 4 (such as a monitor in standard definition (SD), high definition (HD), 4K or higher) displays an image under the control of the signal processing device 6.

An end of the second transmission cable 5 (such as high-definition serial digital interface (HD-SDI), third-generation serial digital interface (3G-SDI), high-definition multimedia interface (HDMI) (registered trademark), or DisplayPort (registered trademark)) is detachably connected to the display device 4, and the other end of the second transmission cable 5 is detachably connected to the signal processing device 6. The second transmission cable 5 transmits a video signal that is processed by the signal processing device 6, to the display device 4.

The signal processing device 6 includes a CPU and the like, and integrally controls the operations of the light source device 22, the camera head 24, and the display device 4.

An end of the third transmission cable 7 is detachably connected to the light source device 22, and the other end of the third transmission cable 7 is detachably connected to the signal processing device 6. The third transmission cable 7 transmits a control signal from the signal processing device 6 to the light source device 22.

Configuration of Signal Processing Device

Next, a configuration of the signal processing device 6 will be described.

In the following, the main part of the present invention will be described as the signal processing device 6.

Figure 2:
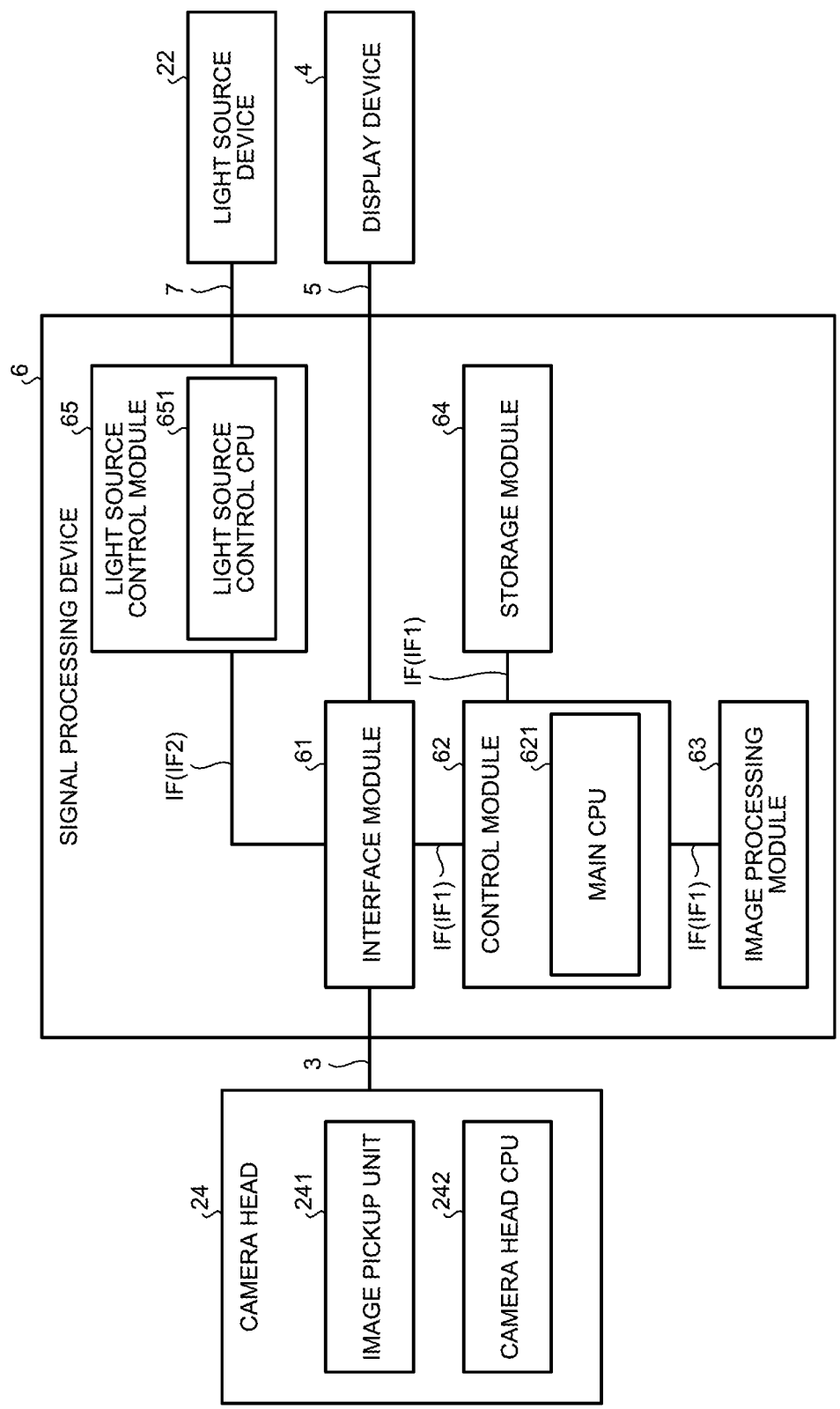
FIG. 2 is a block diagram illustrating a configuration of a signal processing device illustrated in FIG. 1.

FIG. 2 is a block diagram illustrating a configuration of the signal processing device 6.

In FIG. 2, a connector that detachably connects the camera head 24 to the first transmission cable 3, a connector that detachably connects the first transmission cable 3 to the signal processing device 6, a connector that detachably connects the display device 4 to the second transmission cable 5, a connector that detachably connects the second transmission cable 5 to the signal processing device 6, a connector that detachably connects the light source device 22 to the third transmission cable 7, as well as a connector that detachably connects the third transmission cable 7 to the signal processing device 6 are not illustrated. Moreover, in FIG. 2, the electrical wirings and optical fibers that configure the first transmission cable 3 are illustrated as a single cable.

The signal processing device 6 is assembled by using a general personal computer (PC) architecture.

More specifically, as illustrated in FIG. 2, the signal processing device 6 has a configuration in which an interface module 61, a control module 62, an image processing module 63, a storage module 64, and a light source control module 65 are connected using a general interface IF.

Although a specific illustration is omitted, the modules 61 to 65 are disposed inside a casing. After the signal processing device 6 is assembled, tested, and the like, the inside of the casing is set not to open.

The interface IF is an interface the communication protocol and the shape of connectors of which meet a communication interface standard (such as a personal computer/advanced technology (PC/AT) compatible standard).

In the present embodiment, an interface IF1 (IF) for connecting the interface module 61, the control module 62, the image processing module 63, and the storage module 64, is Peripheral Component Interconnect Express (PCIe) (PCI Express (registered trademark)) that is an interface meeting the PC/AC compatible standard. Moreover, a serial peripheral interface (SPI) is used as an interface IF2 (IF) for connecting the interface module 61 with the light source control module 65.

The control module 62 controls the operation of the light source device 22, the operation of the camera head 24, the operation of the display device 4, and the overall operation of the signal processing device 6.

In the present embodiment, the control module 62 includes a motherboard on which a main CPU 621 (FIG. 2) is mounted and that meets the PC/AT compatible standard. The mother mode is provided with expansion slots for connecting to the interface module 61, the image processing module 63, and the storage module 64, respectively.

In this example, the main CPU 621 functions as a first device according to the present invention. In the present embodiment, the main CPU 621 includes a CPU that performs communication according to the PCIe standard.

The interface module 61 functions as a relay device according to the present invention, and is installed into the expansion slot (in the present example, a PCIe slot) provided on the control module 62.

More specifically, the interface module 61 photoelectrically converts an image pickup signal (optical signal) that is input from the camera head 24 via the first transmission cable 3 to an electrical signal, and converts the image pickup signal that is photoelectrically converted, to a digital signal according to the communication interface standard (in the present embodiment, the PCIe standard). The interface module 61 then temporarily stores the converted digital signal in memory (not illustrated) such as a video random access memory (VRAM), and outputs the converted digital signal to the control module 62 via the interface IF1.

The interface module 61 also receives a video signal that is generated by the image processing module 63 from the control module 62 via the interface IF1, and outputs the video signal to the display device 4 via the second transmission cable 5. Upon receiving the video signal, the display device 4 displays an image on the basis of the video signal.

Moreover, the interface module 61 has a relay function of relaying control signal communication between the main CPU 621 that functions as a master, and the camera head CPU 242 as well as a light source control CPU 651 (FIG. 2) of the light source control module 65 that function as slaves relative to the main CPU 621.

The relay function of the interface module 61 will be described below.

For example, the image processing module 63 includes a general-purpose computing on graphics processing unit (GPGPU) and the like, and is installed into the expansion slot (in the present example, the PCIe slot) provided on the control module 62.

More specifically, the image processing module 63 generates a video signal by performing various types of image processing such as a processing procedure, noise reduction, color correction, color emphasis, and contour emphasis on a digital signal (image pickup signal) that is output from the interface module 61 and that is received via the interface IF1 as well as the control module 62. The image processing module 63 then outputs the video signal to the control module 62 via the interface IF1.

For example, the storage module 64 includes a solid state drive (SSD), a hard disk drive (HDD), a dual inline memory module (DIMM), or the like, and is installed into the expansion slot (in the present embodiment, an integrated drive electronics/serial advanced technology attachment (IDE/SATA) connector, and a memory socket) provided on the control module 62.

More specifically, the storage module 64 stores therein programs and an operating system (OS) (such as Windows (registered trademark), Linux (registered trademark), Android (registered trademark), iPhone operating system (iOS) (registered trademark), and real-time operating system (RTOS) (registered trademark)) for causing the image processing module 63 to execute the various types of image processing described above.

The light source control module 65 is connected to the interface module 61 via the interface IF2, and receives the control signal output from the main CPU 621, via the interfaces IF1 and IF2 as well as the interface module 61. The light source control CPU 651 (FIG. 2) that configures the light source control module 65 outputs the control signal to the light source device 22 via the third transmission cable 7, and controls and adjusts the light of the light source device 22 (control and adjust the light supplied to the light guide 23 from the light source device 22).

In this example, the light source control CPU 651 functions as a second device according to the present invention. In the present embodiment, the light source control CPU 651 includes a CPU that performs communication according to the SPI standard.

Relay Function of Interface Module

Next, a relay function of the interface module 61 will be described.

Figure 3:
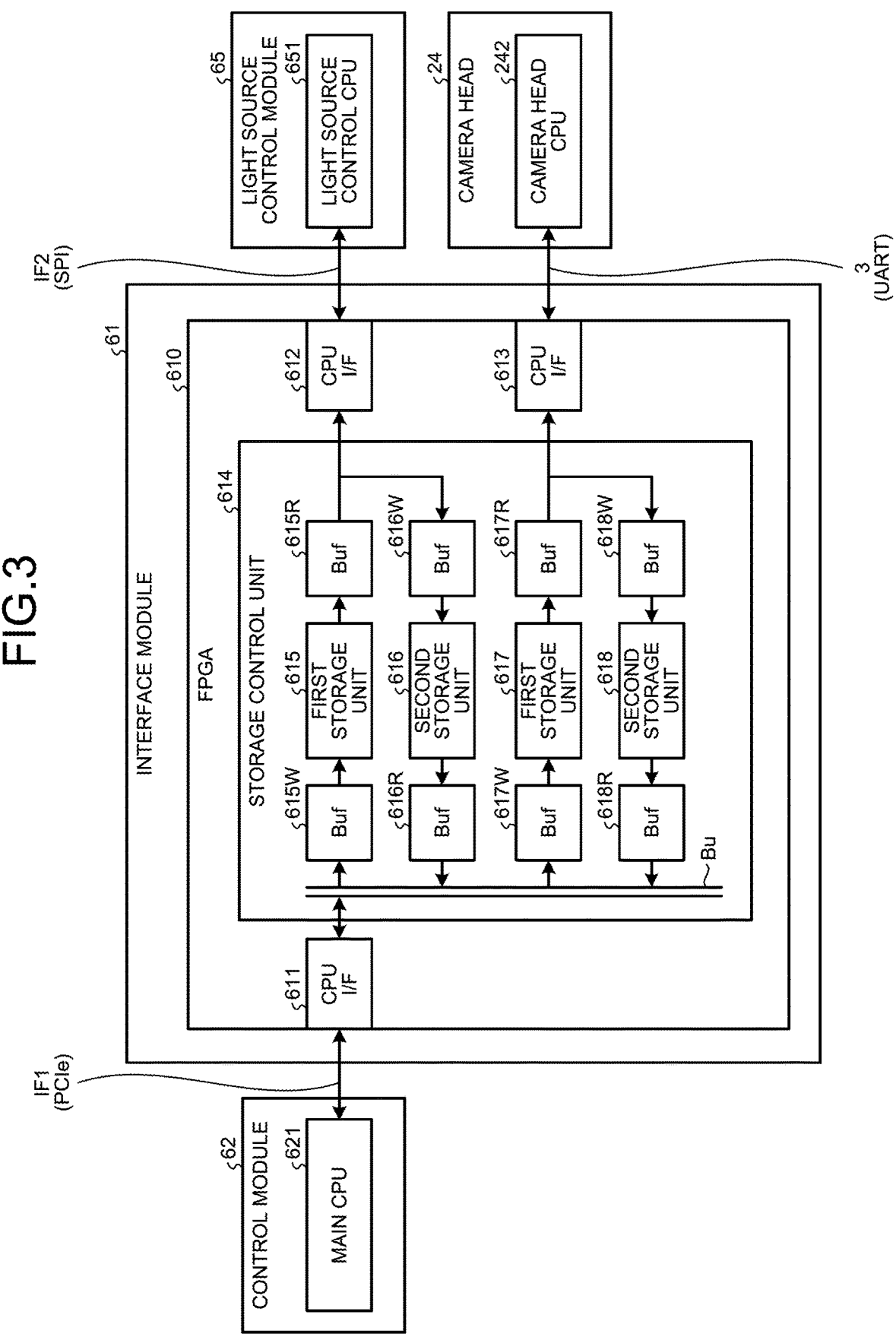
FIG. 3 is a block diagram illustrating a relay function of an interface module illustrated in FIG. 2.

FIG. 3 is a block diagram illustrating a relay function of the interface module 61.

In FIG. 3, similar to that in FIG. 2, the connectors such as the first transmission cable 3 are not illustrated, and the first transmission cable 3 is illustrated as a single cable.

As illustrated in FIG. 3, the interface module 61 includes a field programmable gate array (FPGA) 610 that is a programmable logic device, as the relay function described above.

The FPGA 610 is a logic circuit configured by the control module 62. As illustrated in FIG. 3, the FPGA 610 includes a CPU I/F 611 to a CPU I/F 613, and a storage control unit 614.

The CPU I/F 611 functions as a first interface unit according to the present invention. As illustrated in FIG. 3, the CPU I/F 611 is connected to the main CPU 621 via the interface IF1. The CPU I/F 611 converts (performs protocol conversion on) the control signal (in the present embodiment, the PCIe standard) that is received from the main CPU 621 via the interface IF1 to data that can be processed in the FPGA 610. The CPU I/F 611 also converts (performs protocol conversion on) the data output from the storage control unit 614 to a control signal according to the communication standard of the main CPU 621 (in the present embodiment, the PCIe standard), and transmits the control signal to the main CPU 621 via the interface IF1.

The CPU I/F 612 functions as a second interface unit according to the present invention. As illustrated in FIG. 3, the CPU I/F 612 is connected to the light source control CPU 651 via the interface IF2. The CPU I/F 612 then converts (performs protocol conversion on) the data output from the storage control unit 614 to a control signal according to the communication standard of the light source control CPU 651 (in the present embodiment, the SPI standard), and transmits the control signal to the light source control CPU 651 via the interface IF2. Moreover, the CPU I/F 612 converts (performs protocol conversion on) the control signal (in the present embodiment, the SPI standard) that is received from the light source control CPU 651 via the interface IF2 to data that can be processed in the FPGA 610.

The CPU I/F 613 functions as the second interface unit according to the present invention. As illustrated in FIG. 3, the CPU I/F 613 is connected to the camera head CPU 242 via the first transmission cable 3. The CPU I/F 613 then converts (performs protocol conversion on) the data output from the storage control unit 614 to a control signal according to the communication standard of the camera head CPU 242 (in the present, the UART standard), and transmits the control signal to the camera head CPU 242 via the first transmission cable 3. Moreover, the CPU I/F 613 converts (performs protocol conversion on) the control signal (in the present embodiment, the UART standard) that is received from the camera head CPU 242 via the first transmission cable 3 to data that can be processed in the FPGA 610.

The storage control unit 614 includes first and second storage units 615 and 616 that are used for control signal communication between the main CPU 621 and the light source control CPU 651, as well as first and second storage units 617 and 618 that are used for control signal communication between the main CPU 621 and the camera head CPU 242. In other words, in the present embodiment, the CPU I/F 612 and the CPU I/F 613 are two second interface units according to the present invention. Thus, two pairs of the first and the second storage units 615 (617) and 616 (618) are provided corresponding to the number of the second interface units.

In the present embodiment, the first and the second storage units 615 (617) and 616 (618) include a random access memory (RAM).

The first storage unit 615 temporarily stores therein data (control signal) that is transmitted from the main CPU 621 via the interface IF1, and that is processed by the CPU I/F 611.

In this example, as illustrated in FIG. 3, the storage control unit 614 includes a Buf (buffer) 615W for adjusting the timing at which data is written in the first storage unit 615, and a Buf 615R for adjusting the timing at which data is read out from the first storage unit 615.

The second storage unit 616 temporarily stores therein data (control signal) that is transmitted from the light source control CPU 651 via the interface IF2, and that is processed by the CPU I/F 612.

In this example, as illustrated in FIG. 3, the storage control unit 614 includes a Buf 616W for adjusting the timing at which data is written in the second storage unit 616, and a Buf 616R for adjusting the timing at which data is read out from the second storage unit 616.

Similar to the first storage unit 615, the first storage unit 617 temporarily stores therein data (control signal) that is transmitted from the main CPU 621 via the interface IF1, and that is processed by the CPU I/F 611.

In this example, as illustrated in FIG. 3, the storage control unit 614 includes a Buf 617W for adjusting the timing at which data is written in the first storage unit 617, and a Buf 617R for adjusting the timing at which data is read out from the first storage unit 617.

The second storage unit 618 temporarily stores therein data (control signal) that is transmitted from the camera head CPU 242 via the first transmission cable 3, and that is processed by the CPU I/F 613.

In this example, as illustrated in FIG. 3, the storage control unit 614 includes a Buf 618W for adjusting the timing at which data is written in the second storage unit 618, and a Buf 618R for adjusting the timing at which data is read out from the second storage unit 618.

The FPGA 610 generates a first timing signal TS1 to a fifth timing signal TS5 (see FIG. 4(b) to FIG. 4(f)) on the basis of a reference signal (ST) (see FIG. 4(a)) output from an oscillator (not illustrated).

FIG. 4 is a timing chart illustrating an example of the reference signal ST used in the FPGA 610, and the first timing signal TS1 to fifth timing signal TS5 generated by the FPGA 610.

In FIG. 4, for the sake of convenience, only the rising parts of the reference signal ST and the first timing signal TS1 to fifth timing signal TS5 are illustrated.

The first timing signal TS1 is a timing signal used to communicate between the FPGA 610 and the main CPU 621. As illustrated in FIG. 4(b), the first timing signal TS1 rises at a first timing T1 that is delayed relative to reference timing T0 (FIG. 4(a)) at which the reference signal ST rises, in the same cycle as that of the reference signal ST.

Thus, the FPGA 610 synchronizes with the main CPU 621 by the first timing signal TS1, and communicates with the main CPU 621 at the first timing T1.

The second timing signal TS2 is a timing signal used to transmit the control signal (control signal received from the main CPU 621) to the camera head CPU 242 from the FPGA 610. As illustrated in FIG. 4(*c*), the second timing signal TS2 rises at a second timing T2 that is delayed relative to the first timing T1, in the same cycle as that of the reference signal ST.

The third timing signal TS3 is a timing signal with which the FPGA 610 receives the control signal from the camera head CPU 242. As illustrated in FIG. 4(*d*), the third timing signal TS3 rises at a third timing T3 that is delayed relative to the second timing T2, in the same cycle as that of the reference signal ST.

Thus, the FPGA 610 synchronizes with the camera head CPU 242 by the second timing signal TS2 and the third timing signal TS3, and communicates with the camera head CPU 242 at the second timing T2 and the third timing T3.

The fourth timing signal TS4 is a timing signal used to transmit the control signal (control signal received from the main CPU 621) to the light source control CPU 651 from the FPGA 610. As illustrated in FIG. 4(*e*), the fourth timing signal TS4 rises at a fourth timing T4 that is delayed relative to the second timing T2 and that is early relative to the third timing T3, in the same cycle as that of the reference signal ST.

The fifth timing signal TS5 is a timing signal with which the FPGA 610 receives the control signal from the light source control CPU 651. As illustrated in FIG. 4(*f*), the fifth timing signal TS5 rises at a fifth timing T5 that is delayed relative to the fourth timing T4 and that is early relative to the third timing T3, in the same cycle as that of the reference signal ST.

Thus, the FPGA 610 synchronizes with the light source control CPU 651 by the fourth timing signal TS4 and the fifth timing signal TS5, and communicates with the light source control CPU 651 at the fourth timing T4 and the fifth timing T5.

As described above, in the present embodiment, the first timing T1 and the second timing T2 to fifth timing T5 are set at timings shifted from one another. In other words, the first timing T1 described above corresponds to the first communication timing according to the present invention. The second timing T2 and the fourth timing T4 described above correspond to the second communication timing according to the present invention. Moreover, the third timing T3 and the fifth timing T5 described above correspond to the third communication timing according to the present invention.

In the FPGA 610, the first timing T1 to fifth timing T5 of the generated first timing signal TS1 to fifth timing signal TS5 are changeable according to the setting. In this example, even if the first timing T1 to fifth timing T5 are changed, the first timing T1 and the second timing T2 to fifth timing T5 are set at timings shifted from one another.

Flow of Data in FPGA

Next, flow of data (control signal) in the FPGA 610 at the first timing T1 to fifth timing T5 will be sequentially described.

First Timing

At the first timing T1, the control signal (control signal relative to the camera head CPU 242 and the light source control CPU 651) is transmitted to the FPGA 610 from the main CPU 621 via the interface IF1.

The control signal that is transmitted to the FPGA 610 from the main CPU 621 is converted to data that can be processed in the FPGA 610, in the CPU I/F 611. The storage control unit 614 also temporarily stores the data in the first storage units 615 and 617, via a Bus Bu (FIG. 3) provided inside, as well as the Buf 615W and the Buf 617W, respectively.

Moreover, at the first timing T1, the storage control unit 614 reads out the data stored in the second storage unit 616 (data already stored at the fifth timing T5), and the data stored in the second storage unit 618 (data already stored at the third timing T3), and outputs the data to the CPU I/F 611 via the Buf 616R, the Buf 618R, and the bus Bu. The CPU I/F 611 then converts the data to a control signal according to the communication standard of the main CPU 621 (in the present embodiment, the PCIe standard), and transmits the control signal to the main CPU 621 via the interface IF1.

Second Timing

At the second timing T2, the storage control unit 614 reads out the data stored in the first storage unit 617 (data already stored at the first timing T1 as described above), and outputs the data to the CPU I/F 613 via the Buf 617R. The CPU I/F 613 then converts the data to a control signal according to the communication standard of the camera head CPU 242 (in the present embodiment, the UART standard), and transmits the control signal to the camera head CPU 242 via the first transmission cable 3.

Third Timing

At the third timing T3, the control signal (control signal relative to the main CPU 621) is transmitted to the FPGA 610 from the camera head CPU 242 via the first transmission cable 3.

The control signal that is transmitted to the FPGA 610 from the camera head CPU 242 is converted to data that can be processed in the FPGA 610, in the CPU I/F 613. The storage control unit 614 then temporarily stores the data in the second storage unit 618, via the Buf 618W. As described above, the data (control signal) that is stored in the second storage unit 618 at the third timing T3 is transmitted to the main CPU 621 at the first timing T1.

Fourth Timing

At the fourth timing T4, the storage control unit 614 reads out the data stored in the first storage unit 615 (data already stored at the first timing T1 as described above), and outputs the data to the CPU I/F 612 via the Buf 615R. The CPU I/F 612 then converts the data to a control signal according to the communication standard of the light source control CPU 651 (in the present embodiment, the SPI standard), and transmits the control signal to the light source control CPU 651 via the interface IF2.

Fifth Timing

At the fifth timing T5, the control signal (control signal relative to the main CPU 621) is transmitted to the FPGA 610 from the light source control CPU 651 via the interface IF2.

The control signal that is transmitted to the FPGA 610 from the light source control CPU 651 is converted to data that can be processed in the FPGA 610, in the CPU I/F 612. The storage control unit 614 then temporarily stores the data in the second storage unit 616 via the Buf 616W. As described above, the data (control signal) that is stored in the second storage unit 616 at the fifth timing T5 is transmitted to the main CPU 621 at the first timing T1.

The interface module 61 according to the present embodiment described above relays control signal communication between the main CPU 621 and the light source control CPU 651, and between the main CPU 621 and the camera head CPU 242. The interface module 61 includes the FPGA 610 provided with the CPU I/F 611 to CPU I/F 613 that correspond to the communication standard of the main CPU 621 (in the present embodiment, the PCIe standard), the communication standard of the light source control CPU 651 (in the present embodiment, the SPI standard), and the communication standard of the camera head CPU 242 (in the present embodiment, the UART standard), respectively.

Consequently, when the interface module 61 is used to relay the control signal communication between the main CPU 621 and the light source control CPU 651, and between the main CPU 621 and the camera head CPU 242, the medical observation system 1 can be configured at a low cost, compared to a conventional configuration in which a special device with a plurality of communication interfaces is used. Moreover, it is possible to improve the freedom in selecting a device such as the main CPU 621, while configuring the medical observation system 1.

Moreover, the interface module 61 according to the present embodiment includes two pairs of the first and the second storage units 615 (617) and 616 (618) that are included in each of the CPU I/F 612 and the CPU I/F 613 (light source control CPU 651 and camera head CPU 242). The FPGA 610 relays the control signal between the main CPU 621 and the light source control CPU 651, and between the main CPU 621 and the camera head CPU 242 at the first timing T1 to fifth timing T5, while temporarily storing the control signal in two pairs of the first and the second storage units 615 (617) and 616 (618). Moreover, the first timing T1 and the second timing T2 to fifth timing T5 are set at timings shifted from one another.

Consequently, the timing at which data (control signal) is written into the first and the second storage units 615 (617) and 616 (618), and the timing at which data (control signal) is read out from the first and the second storage units 615 (617) and 616 (618) will not coincide (crash) with each other. In other words, even if the interface module 61 is used to relay data (control signal) between the main CPU 621 and the light source control CPU 651, and between the main CPU 621 and the camera head CPU 242, a communication error will not occur between the main CPU 621 and the light source control CPU 651, and between the main CPU 621 and the camera head CPU 242. Consequently, it is possible to sufficiently achieve communication reliability.

Moreover, in the interface module 61 according to the present embodiment, the first timing T1 to fifth timing T5 of the generated first timing signal TS1 to fifth timing signal TS5 in the FPGA 610 are changeable according to the setting.

Hence, it is possible to set the first timing T1 to fifth timing T5 to appropriate timings according to the processing speed of the main CPU 621, the light source control CPU 651, and the camera head CPU 242 that are connected to the interface module 61, and data amount of the control signal to be transmitted between the main CPU 621 and the light source control CPU 651 and between the main CPU 621 and the camera head CPU 242. In other words, it is possible to further improve the communication reliability between the main CPU 621 and the light source control CPU 651, and between the main CPU 621 and the camera head CPU 242.

Other Embodiments

The mode for carrying out the present invention has been described. However, the present invention is not limited to the embodiment described above.

In the embodiment described above, the medical device according to the present invention is the medical device (medical observation system 1) using a rigid scope (insertion unit 21). However, it is not limited to the above, and a medical device using a flexible scope may also be used. Moreover, the medical device according to the present invention is not limited to the medical device using the rigid scope or the flexible scope, and other medical devices such as an ultrasonic endoscope and a surgical microscope may also be used.

In the embodiment described above, the second device according to the present invention is two devices of the light source control CPU 651 and the camera head CPU 242. However, the number of the second device is not limited to two, and may be one or may be three or more. When the number of the second device according to the present invention is set to one or set to three or more, the number of the second interface units (CPU I/F 612 and CPU I/F 613) according to the present invention, and the number of the pair of the first and the second storage units (first and second storage units 615 (617) and 616 (618)) according to the present invention may be provided as many as the second device.

The second device according the present invention is not limited to the light source control CPU 651 or the camera head CPU 242, and a CPU included in other peripheral devices may also be used.

Furthermore, the second device according to the present invention is not limited to the CPU, and an image pickup element such as the FPGA and CMOS sensor, or a motor may also be used.

In the embodiment described above, the second timing T2 to fifth timing T5 are set at timings shifted from one another. However, as long as the first timing T1 and the second timing T2 to fifth timing T5 are set at timings shifted from one another, at least one of the second timing T2 to fifth timing T5 may be set at the same timing.

In the embodiment described above, the FPGA 610 is used as the programmable logic device according to the present invention. However, it is not limited thereto, and a complex programmable logic device (CPLD) or the like may also be used.

Moreover, in the embodiment described above, the first and the second storage units 615 (617) and 616 (618) are provided inside the programmable logic device. However, it is not limited thereto, and the first and the second storage units 615 (617) and 616 (618) may be provided outside the programmable logic device.

In the embodiment described above, the storage control unit 614 may switch the banks of the first and the second storage units 615 (617) and 616 (618). By switching the banks in this manner, it is possible to expand the RAM area, and store the past data and special data in the first and the second storage units 615 (617) and 616 (618).

In the embodiment described above, the PCIe is used as the interface IF1. However, the interface IF1 is not limited to the PCIe, and a Universal Serial Bus (USB), an Ethernet (registered trademark), a Serial ATA (SATA), a HDMI (registered trademark), an Institute of Electrical and Electronic Engineers (IEEE) 1394 (registered trademark), a DisplayPort (registered trademark), a recommended standard 232 version C (RS 232C), a General Purpose Input/Output (GPIO), and the like may also be used. Moreover, the interface IF2 is not limited to the SPI, and the other communication interface may also be used.

In the embodiment described above, the communication standard of the main CPU 621 is the PCIe, the communication standard of the light source control CPU 651 is the SPI standard, and the communication standard of the camera head CPU 242 is the UART standard. However, it is not limited thereto, and the other communication standard may also be used.

REFERENCE SIGNS LIST

- 1 medical observation system
- 2 endoscope
- 3 first transmission cable
- 4 display device
- 5 second transmission cable
- 6 signal processing device
- 7 third transmission cable
- 21 insertion unit
- 22 light source device
- 23 light guide
- 24 camera head
- 61 interface module
- 62 control module
- 63 image processing module
- 64 storage module
- 65 light source control module
- 241 image pickup unit
- 242 camera head CPU
- 610 FPGA
- 611 to 613 CPU I/F
- 614 storage control unit
- 615, 617 first storage unit
- 616, 618 second storage unit
- 615R to 618R, 615W to 618W Buf
- 621 main CPU
- 651 light source control CPU
- Bu bus
- IF, IF1, IF2 interface
- ST reference signal
- T0 reference timing
- T1 to T5 first to fifth timings
- TS1 to TS5 first to fifth timing signals

The invention claimed is:

1. A relay device for being used in a medical device including a first device and a plurality of second devices, the second devices each performing control signal communication with the first device, and for relaying the control signal communication between the first device and the second devices, the relay device comprising:
   a programmable logic device including:
   a first interface configured to communicate with the first device in a communication scheme corresponding to a communication scheme of the first device; and
   a plurality of second interfaces each configured to perform communication with the respective second devices in communication schemes corresponding to communication schemes of the second devices; and
   a plurality of pairs of a first memory and a second memory, wherein the pairs of the first memory and the second memory are provided in each of the second interfaces,
   the programmable logic device temporarily stores a first control signal received from the first device via the first interface in the first memory at a first communication timing, and transmits the first control signal to the second device via the second interface at a second communication timing, and temporarily stores a second control signal received from the second device via the second interface in the second memory at a third communication timing, and transmits the second control signal to the first device via the first interface at the first communication timing, and the first communication timing and the second and the third communication timings are set at timings shifted from one another, and the first communication timing, the second communication timing, and the third communication timing are changeable according to a setting stored in the programmable logic device,
   wherein the setting is set according to processing speeds in the first device and the plurality of second devices, and wherein the setting is further set according to a data amount of the control signal communication.

2. A medical device, comprising:
   a first device;
   a plurality of second devices that each perform control signal communication with the first device; and
   a relay device that includes
   a programmable logic device including:
   a first interface configured to communicate with the first device in a communication scheme corresponding to a communication scheme of the first device, and a plurality of second interfaces each configured to perform communication with the respective second devices in communication schemes corresponding to communication schemes of the second devices, and
   a plurality of pairs of a first memory and a second memory, wherein the pairs of the first memory and the second memory are provided in each of the second interfaces,
   the programmable logic device
   temporarily stores a first control signal received from the first device via the first interface in the first memory at a first communication timing, and transmits the first control signal to the second device via the second interface at a second communication timing, and
   temporarily stores a second control signal received from the second device via the second interface in the second memory at a third communication timing, and transmits the second control signal to the first device via the first interface at the first communication timing, and
   the first communication timing and the second and the third communication timings are set at timings shifted from one another, and the first communication timing, the second communication timing, and the third communication timing are changeable according to a setting stored in the programmable logic device,
   wherein the setting is set according to processing speeds in the first device and the plurality of second devices, and wherein the setting is further set according to a data amount of the control signal communication.

3. The relay device according to claim 1, wherein the pairs of the first memory and the second memory are provided in each of the second interfaces and are provided inside the programmable logic device.

* * * * *